(12) United States Patent
Pohjanvesi et al.

(10) Patent No.: US 6,677,478 B2
(45) Date of Patent: Jan. 13, 2004

(54) PROCESS FOR THE PRODUCTION OF PERCARBOXYLIC ACID

(75) Inventors: Seppo Pohjanvesi, Oulu (FI); Eva-Liisa Mustonen, Oulu (FI); Arto Pukkinen, Kempele (FI); Reino Lehtinen, Espoo (FI)

(73) Assignee: Kemira Chemicals Oy, Helsinki (FI)

( * ) Notice: Subject to any disclaimer, the term of this patent is extended or adjusted under 35 U.S.C. 154(b) by 0 days.

(21) Appl. No.: 10/114,295

(22) Filed: Apr. 3, 2002

(65) Prior Publication Data

US 2002/0177732 A1 Nov. 28, 2002

(30) Foreign Application Priority Data

Apr. 4, 2001 (FI) .............................................. 20010706

(51) Int. Cl.$^7$ ............................................. C07C 409/26
(52) U.S. Cl. ................................................ 562/6; 562/4
(58) Field of Search ...................... 562/2, 4, 6

(56) References Cited

U.S. PATENT DOCUMENTS 4,904,821 A  2/1990  Boehme et al.

FOREIGN PATENT DOCUMENTS

| EP | 0 789 016 B1 | 6/1998 |
| EP | 1 004 576 A1 | 5/2000 |
| FR | 1432773 | 6/1966 |
| GB | 1014361 | 3/1963 |

OTHER PUBLICATIONS

CA:126:28035 abs of JP08268807 Oct. 1996.*

* cited by examiner

*Primary Examiner*—Jean F. Vollano
(74) *Attorney, Agent, or Firm*—Young & Thompson

(57) ABSTRACT

The conventional process for the production of a peracetic acid product, wherein hydrogen peroxide, acetic acid and water are fed into an aqueous reaction medium containing hydrogen peroxide, acetic acid, peracetic acid and an acid catalyst, wherein hydrogen peroxide and acetic acid react in the presence of the acid catalyst and form peracetic acid, and an aqueous peracetic acid concentrate is removed continuously from the reaction medium by distillation, has now been improved by feeding the acid catalyst continuously into the reaction medium and by withdrawing continuously a portion of the reaction medium as a bottom product. When the through flow of the reaction medium is thus increased, it is purified of impurities threatening the safety of the process. If the amount of acid catalyst in the reaction medium is further decreased, a product suitable, for example, for disinfection is obtained from the bottom product.

19 Claims, 1 Drawing Sheet

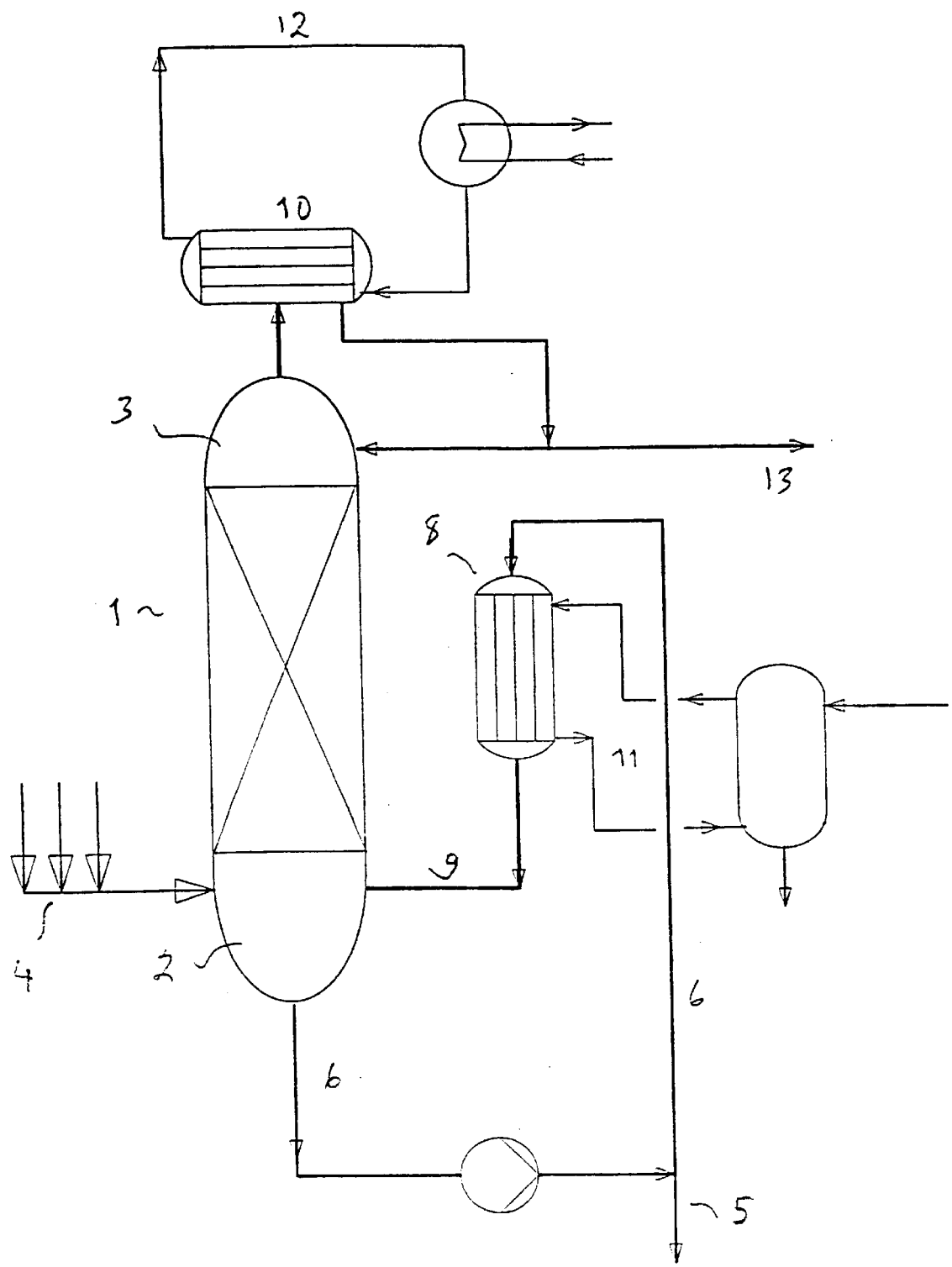

PROCESS FOR THE PRODUCTION OF PERCARBOXYLIC ACID

FIELD OF THE INVENTION

The invention relates to a process for the production of a percarboxylic acid product, e.g. a peracetic acid product and a perpropionic acid product, by feeding hydrogen peroxide, acetic acid and water continuously into an aqueous reaction medium containing hydrogen peroxide, acetic acid, percarboxylic acid and an acid catalyst, wherein hydrogen peroxide and acetic acid react in the presence of an acid catalyst and form percarboxylic acid, and by removing an aqueous percarboxylic acid concentrate continuously from the reaction medium by distillation.

The invention also relates to a percarboxylic acid product of the above type and its use for combating microorganisms.

STATE OF THE ART

Below, the concentration percentages used in the specification of the invention indicate percentages by weight. Additionally there are used acronyms AA=acetic acid, PAA=peracetic acid, dPAA=distilled peracetic acid, ePAA=equilibrium mixture.

The conventional process for producing percarboxylic acid, such as peracetic acid, is based on an equilibrium reaction between it and water and between acetic acid and hydrogen peroxide, in a reaction medium:

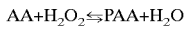

The catalyst used in this case is a strong mineral acid, the most common being sulfuric acid. The equilibrium mixture is prepared simply by mixing the components together. The composition of the equilibrium mixture depends, among other things, on the molar ratio of the starting materials.

Stronger and purer aqueous solutions of percarboxylic acid are in general produced by distilling percarboxylic acid from the reaction medium under a reduced pressure and at an elevated temperature. Thereby an aqueous percarboxylic acid concentrate is obtained, which contains percarboxylic acid, water and in general a small amount of carboxylic acid and possibly a very small amount of hydrogen peroxide.

Patent publication EP 0 789 016 A1 discloses a process for the production of peracetic acid. In the process, hydrogen peroxide and acetic acid are allowed to react in an aqueous solution that contains hydrogen peroxide, acetic acid, peracetic acid, sulfuric acid and a stabilizer (phosphonic acid). The equilibrium mixture contains 3–12% of PAA, 1–8% of AA, and 10–35% of $H_2O_2$. The molar ratio of hydrogen peroxide to acetic acid in the equilibrium mixture is within the range 4–30. The reaction solution additionally contains sulfuric acid 10–25%. There prevails a reduced pressure in the reactor, and the equilibrium mixture is heated so that the peracetic acid and the water vaporize and leave the reaction mixture. The vapor phase is directed to a distillation column, where peracetic acid concentrates relative to the other components. The peracetic acid vapor is directed from the distillation column to a condenser, where the peracetic acid condenses to an aqueous solution having a PAA concentration of 20–60%. A portion of the solution is removed into the product container and a portion is returned to the distillation column.

U.S. Pat. No. 4,904,821 discloses a process for the production of peracetic acid so that the peracetic acid is in an organic solvent. In the production process the molar ratio of hydrogen peroxide to acetic acid is 1–2. The hydrogen peroxide is fed into the reactor as a 30–35% aqueous solution so that the weight ratio of hydrogen peroxide to water is 0.42–0.54. The amount of sulfuric acid is 20–30% of the weight of the entire equilibrium mixture. The temperature is within the range 55–70° C. and the pressure is 100–200 mbar. The vapor phase formed in the reaction, containing peracetic acid, acetic acid and water, is directed to the absorption zone into contact with an organic phosphate circulating in the opposite direction, whereupon a portion of the peracetic acid and acetic acid passes into the organic solvent.

The sulfuric acid amounts presented in the above-mentioned patent publications are highly typical of the production technology currently used. The acid catalyst speeds up the reaction between carboxylic acid and hydrogen peroxide and the formation of an equilibrium mixture.

Patent publication GB 1 014 361 discloses results of tests aimed at determining how much sulfuric acid is required in the reaction mixture. It is evident from the results presented in the table of the patent publication that, if sulfuric acid is used in an amount of 1%, the PAA concentration in the distillate remains low and the retention time of the reaction is more than three times that in tests in which sulfuric acid was used in an amount of 9–20%. On the other hand, if sulfuric acid is used in an amount higher than 20%, it is necessary to add water to the reaction mixture. In this case the sulfuric acid and water take up too large a proportion of the reactor volume, and the amount of product per unit volume of the reactor decreases. On the basis of these tests, the patent publication presents a process for the production of peracetic acid wherein hydrogen peroxide and acetic acid, the molar ratio of which is 0.3–5, are allowed to react in a reaction mixture containing sulfuric acid 5–20% and water 20–75%, at a temperature of 20–80° C. and a pressure of 15–350 mmHg. The reaction product vaporizing out from the mixture, the product containing PAA, AA and water, is directed to a condenser and is recovered.

In the production of distilled percarboxylic acid the reaction medium contains large amounts of sulfuric acid and metallic impurities. Impurities accumulate in the reaction medium, and therefore the medium is removed at predetermined times as a bottom product when the amount of impurities grows too large. In conventional production processes this is an unusable waste, and so attempts have been made to maintain the amount of the solution to be removed as small as possible. The metallic impurities are derived mainly from the carboxylic acid and the hydrogen peroxide. Metallic impurities are detrimental, since, among other things, they decompose hydrogen peroxide.

Conventionally the bottom product has thus been a waste unusable owing to the large amounts of sulfuric acid and impurities present in it. In the conventional process there is additionally always the risk that so large amounts of metallic impurities accumulate in the bottom product that they tend to decompose the percarboxylic acid solution, and a dangerously rapid increase in pressure may result.

SUMMARY OF THE INVENTION

Thus there is in the field a clear need for a production process wherein, on the one hand, the bottom product could be used as such and, on the other hand, the production process would be safe. In this case the improving of the usability of the bottom product would at the same time improve the profitability of the entire production process.

BRIEF DESCRIPTION OF THE DRAWINGS

FIG. 1 shows diagrammatically the process used in the production of peracetic acid.

DETAILED DESCRIPTION OF THE INVENTION

The object of the invention is thus to provide a continuous process for the production of percarboxylic acid wherein the efficiency ratio of the raw materials would be maximally high, i.e. to produce a usable bottom product. An additional object is a safe process for the production of percarboxylic acid products.

These objects can be achieved with the continuous process for the production of percarboxylic acid, described above, which process is mainly characterized in that the acid catalyst is fed continuously into the reaction medium so that the amount of acid catalyst in the reaction medium is kept at an interval which corresponds to 0,5–10% by weight of sulfuric acid and from the reaction medium is continuously withdrawn 1–10% by weight of the total amount of the materials fed in as a bottom product as a bottom product. It has thus been realized that by means of the said continuous feeding in and withdrawal the impurities can be rinsed out from the reaction medium. Thus the production process according to the invention produces two usable mixtures. When the bottom product is withdrawn continuously into a product storage, the impurities accumulated at the bottom of the reaction vessel are removed and their concentration in the reaction medium remains low. This improves the safety of the production process. On the other hand, the bottom product removed has smaller amounts of impurities and it is thus usable.

The present process is suited for the production of all kinds of percarboxylic acids, such as perpropionic acid and peracetic acid. However, the process is at its most advantageous in the production of peracetic acid.

The invention, for its part, is based on the continuous withdrawing of the reaction medium from the bottom of a column or the like, in which case both the reaction medium and the bottom product are purer. In the process it is advantageous to maintain a stationary state, wherein the feed amount and composition, the composition of the reaction medium, and the withdrawn amounts and compositions are maintained substantially constant. This means, among other things, that there is added to the reaction mixture as much acid catalyst as is removed in the bottom product. In general the equilibrium reaction between carboxylic acid and hydrogen peroxide, and percarboxylic acid and water, is allowed to determine the composition of the reaction medium.

The bottom product can be removed in the desired amount. The larger the amount of bottom product withdrawn, the purer the reaction medium and the bottom product itself. Preferably the bottom product is withdrawn in an amount of 3–5% by weight, of the total amount of the materials fed in.

As stated above, a large amount of acid catalyst in the bottom product reduces its usability. Thus in the process of the present application it is advantageous to maintain the acid catalyst amount in the reaction medium within a range the pH value of which corresponds to a sulfuric acid concentration of 1–5% by weight, most preferably 2–3% by weight. It has namely been observed that the reducing of the acid catalyst amount does not necessarily reduce the concentration of percarboxylic acid in the distillate in the manner stated in GB 1 014 361; this can be affected, for example, by increasing the concentration of percarboxylic acid in the reaction medium. Cf. the recommended concentrations below. Furthermore, the distillation operation can be made more effective by various means.

The acid catalyst is in general an inorganic acid or a mixture thereof, the inorganic acid being preferably phosphoric acid or sulfuric acid, most preferably sulfuric acid.

The process according to the invention works better in the production of peracetic acid if there is maintained in the reaction medium a molar ratio of acetic acid to water that is above approximately 0.12, preferably above approximately 0.15, preferably at least approximately 0.20. At the same time the preferred acetic acid concentration in the reaction medium is 10–40% by weight, most preferably 20–30% by weight.

A preferred molar ratio of hydrogen peroxide to acetic acid in the reaction medium is 0.5:1–5:1, and most preferably approximately 1:1. It is at the same time preferable to maintain in the reaction medium a hydrogen peroxide concentration of 10–30% by weight, preferably 15–25% by weight. The concentration of peracetic acid in the reaction medium is preferably 5–30% by weight, preferably 10–20% by weight.

As stated, the continuous feeding in of acid catalyst and continuous withdrawing of bottom product are carried out in a percarboxylic process wherein a percarboxylic acid concentrate is withdrawn continuously from the reaction medium by distillation. In the production of peracetic acid, the distillation is preferably carried out so that the peracetic acid concentration in the concentrate is 20–70% by weight, more preferably so that the said concentration is 30–60% by weight, and most preferably so that it is 35–50% by weight. The distillation temperature is typically adjusted to a value of 40–80° C., preferably a value of 45–55° C., and the distillation pressure is typically adjusted to a value of 40–100 mbar, preferably a value of 50–70 mbar.

The invention also relates to a peracetic acid product which can be produced by the above process, by recovering the said bottom product. Thus the peracetic acid product according to the invention is characterized in that it contains 10–20% by weight of peracetic acid, 10–30% by weight of hydrogen peroxide, 20–30% by weight of acetic acid, 1–5% by weight of sulfuric acid or any other inorganic acid or acid mixture corresponding to its pH value, and water.

Compared with the state of the art, the peracetic acid product according to the present invention contains less sulfuric acid or the like, and larger amounts of the initial substances and peracetic acid. Furthermore, owing to the through-flow according to the invention, the peracetic acid product does not contain as large amounts of metallic impurities such as iron and chromium as do the bottom products according to the state of the art.

Finally the invention relates to the use, for combating microorganisms, of a peracetic acid product which contains 10–20% by weight of peracetic acid, 10–30% by weight of hydrogen peroxide, 20–30% by weight of acetic acid, 1–5% by weight of sulfuric acid or any other inorganic acid or acid mixture corresponding to its pH value, and water.

It has also been observed that the bottom product is usable for disinfection applications, the removal of odors, and the destruction of detrimental microbes. Thus it need not be thrown away as in conventional production processes, in which the amounts of sulfuric acid and metals in the bottom product are so high that the bottom product is not suitable for use for the said applications.

The invention is described below in greater detail, with reference to the accompanying figure, which shows diagrammatically the process used in the production of peracetic acid.

The production takes place in a distillation column 1, to the bottom 2 of which there are fed the raw materials of the equilibrium solution: acetic acid, hydrogen peroxide, water, and sulfuric acid serving as a catalyst. In addition the solution contains dipicolinic acid as a stabilizer. The equilibrium solution is diluted with water so that the distillate comes out at the correct concentration. Sulfuric acid is fed to the bottom of the distillation column in an amount equal to that taken out in the bottom product. A reduced pressure and a temperature of approximately 45–55° C. prevail in the column 1. The raw materials react at the bottom 2 of the column and form peracetic acid and water. Peracetic acid and water are distilled out as a distillate from the equilibrium solution from the upper end 3 of the column. Some acetic acid is carried in the distillate. At the bottom of the column there accumulate metallic impurities (e.g. iron and chromium), which enter in the acetic acid and hydrogen peroxide. These impurities leave along with the bottom product. The amount of bottom product withdrawn is 3–5% of the amount of the equilibrium solution. An amount of fresh sulfuric acid corresponding to the amount of sulfuric acid leaving in the bottom product is added to the raw material feed 4, as mentioned above, in order that its concentration should remain at the correct value. Equilibrium solution is pumped via line 6 with a pump to the upper part of the vaporizer 8. The vaporizer 8 has pipes on the inner surfaces of which the solution flows and heats up. The pipes are heated from the outside with a saturated water vapor having a temperature of 70–80° C. and a pressure below 1 bar. From the vaporizer 8 the heated solution and vapor flow back to the bottom of the column via connection 9.

The separation takes place in the packing bed of the column, and the vapor is condensed in a condenser 10, from which all of it is withdrawn. A portion of the distillate is taken out as a product from line 13, and a portion is returned to the column in order that a sufficient degree of purity should be obtained for the product. By return ratio is meant the weight ratio of the distillate to the condensate returned. The condenser 8 is cooled using a closed cooling water cycle, in which pure water is used. The pure water travels via a cooler.

The bottom product contains 10–15% of peracetic acid, 25% of acetic acid and 20% of hydrogen peroxide and approximately 3% of sulfuric acid. The product contains 40% of peracetic acid and less than 4% of acetic acid and less than 2% of hydrogen peroxide. The produce is cooled in order that it should not decompose to its raw materials. The product is stored in a cold storage.

EXAMPLE

The process described above was used in continuous production of peracetic acid. The temperature of the distillation column was within the range 45–55° C. and its pressure 50–70 mbar. Bottom solution was withdrawn in an amount of 2–4%, calculated from the total amount of the materials fed in as raw materials.

The analysis of the distilled solution (dPAA) was:

| PAA | 44.6% |
|---|---|
| AA | <1% |

The analysis of the bottom product (ePAA) was:

| PAA | 15.0% |
|---|---|
| AA | 25.2% |
| $H_2O_2$ | 18.9% |
| $H_2SO_4$ | 2.2% |
| Metals | 2.5 ppm |

The basic idea of the invention is that, contrary to what has been believed previously, percarboxylic acid can be produced continuously with a very small amount of acid catalyst without the retention time increasing substantially. A smaller amount of catalyst reduces the reaction velocity, but on the other hand the retention time can be affected in very many ways, as pointed out earlier. The small amount of acid catalyst and impurities makes the bottom product a usable product. Respectively, when bottom product is withdrawn continuously in an amount of 3–5% of the amount of the raw materials fed in, the amounts of impurities in the column are smaller and the safety of the process is improved. Thus the invention improves not only the economy but also the safety of the production process.

What is claimed is:

1. A process for the production of a peracetic acid product by feeding hydrogen peroxide, acetic acid and water continuously into an aqueous reaction medium containing hydrogen peroxide, acetic acid, peracetic acid and an acid catalyst, wherein said hydrogen peroxide and acetic acid react in the presence of the acid catalyst to form peracetic acid, and removing an aqueous peracetic acid concentrate continuously from the reaction medium by distillation, comprising continuously feeding an acid catalyst into the reaction medium so that the amount of acid catalyst in the reaction medium is kept at an interval which corresponds to 0.5–10% by weight of sulfuric acid, and continuously withdrawing 1–10% by weight of the reaction medium as the bottom product.

2. The process according to claim 1, wherein a stationary state is maintained so that the amount and composition of the feed, the composition of the reaction medium, and the amounts and compositions withdrawn are maintained substantially constant.

3. The process according to claim 1, wherein the amount of acid catalyst in the reaction medium is maintained within 50% of a range so that the pH value of the reaction medium corresponds to a sulfuric acid concentration of 1–5% by weight of the reaction medium.

4. The process according to claim 1, wherein the acid catalyst is an inorganic acid or a mixture thereof, the inorganic acid being phosphoric acid or sulfuric acid.

5. The process according to claim 1, wherein there is maintained in the reaction medium an acetic acid to water molar ratio which is above approximately 0.12.

6. The process according to claim 1, wherein there is maintained in the reaction medium an acetic acid concentration of 10–40% by weight.

7. The process according to claim 1, wherein there is maintained in the reaction medium a hydrogen peroxide to acetic acid molar ratio of 0.5:1–5:1.

8. The process according to claim 1, wherein there is maintained in the reaction medium a hydrogen peroxide concentration of 10–30% by weight.

9. The process according to claim 1, wherein there is maintained in the reaction medium a peracetic acid concentration of 5–30% by weight.

10. The process according to claim 1, wherein an aqueous peracetic acid concentrate is removed from the reaction medium continuously by distillation so that the peracetic acid concentration in the concentrate is 20–70% by weight.

11. The process according to claim 1, wherein the distillation temperature is adjusted to a value of 40–80° C., and the distillation pressure is adjusted to a value of 40–100 mbar.

12. The process according to claim 1, wherein said product of the reaction medium is determined according to the equilibrium state of said reaction.

13. The process according to claim 4, wherein said acidic acid to water molar ratio is above approximately 0.15.

14. The process according to claim 6, wherein there is maintained in the reaction medium an acetic acid concentration of 20–30%.

15. The process according to claim 7, wherein said hydrogen peroxide to acidic acid molar ratio is approximately 1:1.

16. The process according to claim 8, wherein said hydrogen peroxide concentration is 15–25% by weight.

17. The process according to claim 9, wherein said peracetic acid concentration is 10–20% by weight.

18. The process according to claim 10, wherein said peracetic acid concentration is 30–60% by weight.

19. The process according to claim 11, wherein said distillation temperature is adjusted to a value of 45–55° C., and the distillation pressure is adjusted to a value of 50–70 mbar.

* * * * *